(12) United States Patent
Carlsson (10) Patent No.: US 11,383,484 B2
(45) Date of Patent: Jul. 12, 2022

(54) COMPOSITE MATERIAL FOR FLUID FLOW MANAGEMENT

(71) Applicant: Mölnlycke Health Care AB, Gothenburg (SE)

(72) Inventor: Erik Carlsson, Särö (SE)

(73) Assignee: Mölnlycke Health Care AB, Gothenburg (SE)

( * ) Notice: Subject to any disclaimer, the term of this patent is extended or adjusted under 35 U.S.C. 154(b) by 352 days.

(21) Appl. No.: 16/495,250

(22) PCT Filed: Apr. 3, 2018

(86) PCT No.: PCT/EP2018/058477
§ 371 (c)(1),
(2) Date: Sep. 18, 2019

(87) PCT Pub. No.: WO2018/185092
PCT Pub. Date: Oct. 11, 2018

(65) Prior Publication Data
US 2021/0129483 A1    May 6, 2021

(30) Foreign Application Priority Data

Apr. 5, 2017   (EP) .................................. 17165060

(51) Int. Cl.
*B32B 5/24* (2006.01)
*A61F 13/00* (2006.01)
(Continued)

(52) U.S. Cl.
CPC ........ *B32B 5/245* (2013.01); *A61F 13/00012* (2013.01); *A61F 13/00017* (2013.01);
(Continued)

(58) Field of Classification Search
CPC .. B32B 5/245; B32B 5/18; B32B 7/12; B32B 23/048; B32B 5/022; A61F 13/00029; A61F 13/00012; A61L 15/26; A61L 15/60
See application file for complete search history.

(56) References Cited

U.S. PATENT DOCUMENTS 5,977,014 A    11/1999   Plischke et al.
2004/0126413 A1   7/2004   Sigurjonsson et al.
(Continued)

FOREIGN PATENT DOCUMENTS

DE    102014106518 A1    11/2015

OTHER PUBLICATIONS

International Search Report and Written Opinion were dated May 4, 2018 by the International Searching Authority for International Application No. PCT/EP2018/058477, filed on Apr. 3, 2018 and published as WO 2018/185092 on Oct. 11, 2018 (Applicant—Mölnlycke Health Care AB) (9 Pages).

*Primary Examiner* — Hai Vo
(74) *Attorney, Agent, or Firm* — Ballard Spahr LLP (57) ABSTRACT

A composite material (and its manufacture) is described that has (i) a first layer comprising an absorbent fiber material that is in contact with the area of use on its first side, (ii) a second layer comprising an absorbent material, said second layer being arranged on the second side of said first layer, wherein a plurality of channels extends through the entire first layer, from said first side to said second side thereof, and further extends into at least a portion of said second layer. This composite is of particular use in wound treatment.

15 Claims, 3 Drawing Sheets

(51) Int. Cl.

| | |
|---|---|
| *A61F 13/36* | (2006.01) |
| *A61L 15/26* | (2006.01) |
| *A61L 15/42* | (2006.01) |
| *A61L 15/60* | (2006.01) |
| *B32B 5/02* | (2006.01) |
| *B32B 7/12* | (2006.01) |
| *B32B 23/04* | (2006.01) |
| *B32B 5/18* | (2006.01) |

(52) U.S. Cl.
CPC ........ *A61F 13/00029* (2013.01); *A61F 13/36* (2013.01); *A61L 15/26* (2013.01); *A61L 15/425* (2013.01); *A61L 15/60* (2013.01); *B32B 5/022* (2013.01); *B32B 5/18* (2013.01); *B32B 7/12* (2013.01); *B32B 23/048* (2013.01); B32B 2255/02 (2013.01); B32B 2262/0223 (2013.01); B32B 2262/0246 (2013.01); B32B 2262/04 (2013.01); B32B 2262/062 (2013.01); B32B 2266/0278 (2013.01); B32B 2266/122 (2016.11); B32B 2305/022 (2013.01); B32B 2305/20 (2013.01); B32B 2307/728 (2013.01); B32B 2535/00 (2013.01); B32B 2556/00 (2013.01)

(56) References Cited

U.S. PATENT DOCUMENTS

| | | | |
|---|---|---|---|
| 2004/0241214 A1* | 12/2004 | Kirkwood | A61F 13/0263 424/445 |
| 2016/0317353 A1* | 11/2016 | Wang | A61F 13/00017 |
| 2017/0143552 A1* | 5/2017 | Hartwell | A61F 13/0233 |

* cited by examiner

COMPOSITE MATERIAL FOR FLUID FLOW MANAGEMENT

CROSS-REFERENCE TO RELATED APPLICATIONS

This application is a U.S. National Phase Application of International Application No. PCT/EP2018/058477, filed Apr. 3, 2018, which claims priority to European Application No. 17165060.9, filed Apr. 5, 2017, each of which are hereby incorporated by reference in their entirety.

BACKGROUND OF THE INVENTION

Fluid management, including directing a flow of fluids, is of particular importance in a variety of applications, for example for personal hygiene articles, cleaning systems, air and moisture control, as well as in skin and wound care and treatment.

In particular in wound care, hydrophilic materials are routinely used in wound dressings to absorb and retain wound fluids, further particularly hydrophilic foams such as hydrophilic open-cell polyurethane foams. Hydrophilic fibers such as hydrophilic cellulosic fibers, are also known, in principle, to be useful in wound treatment and may also be used in fluid management/liquid handling. In the following, while the focus in terms of application is on wound care and treatment, the composite materials of the present invention may be used in all other conceivable areas of application, including the specific areas of application as outlined above.

To optimize liquid handling capacity, the wound pad in a wound dressing may preferably include a composite material, in particular a multiple-layer arrangement, wherein each layer preferably is of a different material thus providing different capabilities and functionalities. To the extent such multiple-layer arrangements are known from the art, the layers are typically laminated by means of an adhesive and/or by mechanical lamination. Lamination or even simple "bringing into contact" of two layers creates an interface.

Such an interface may exist, for example, between a fiber layer that is in immediate contact with (proximate to) a wound, and which is optimized to transport wound exudate away from the wound, and an adjacent foam layer that is in immediate contact with said fiber layer, but farther away from the wound. Said foam layer is typically optimized to store liquid sufficiently away from the wound. Said interface between these two layers, however, creates a hindrance to fluid flow and therefore a hindrance to transporting wound exudate away from the wound (and the fiber layer in immediate contact therewith), to the foam storage layer.

In a clinical environment this might mean that not sufficient fluid is transferred to the foam layer, causing the complete dressing to leak when the gel forming fiber layer has reached its maximum absorption. This may also lead to maceration of the surrounding skin due to wetting of the same.

As an example of such multi-layer structure comprising laminated interfaces, U.S. Pat. No. 7,759,537 discloses a multi-layer wound dressing including inter alia a wound contacting layer and an absorbent core layer, wherein a "keying layer" of a polyamide web, which is a hot melt adhesive, is provided on the absorbent core layer to bind the absorbent core layer to the wound contact layer. Similarly, EP 2 659 865 discloses a multiple-layer wound dressing comprising inter alia a nonwoven layer sandwiched between two foam layers, wherein all layers can be bonded together using heat activated bonding webs. These "keying" or "bonding" layers have the tendency to limit or reduce, or at least hinder fluid flow from the wound to the storage area.

These problems associated with the existence of an interface between two layers are exacerbated in case the fiber layer comprises fibers that swell when in contact with a fluid, for example a wound exudate. In particular, hydrophilic fibers as used in the ultimate vicinity of the wound have the capacity to take up large amounts of fluid so that the fibers ultimately form a hydrogel and swell to the extent that internal channels and void structures used to lead fluid away from the wound may be partially or fully blocked, thus further hindering fluid flow from the wound toward the foam storage layer.

SUMMARY OF THE INVENTION

In view of the above-mentioned and other drawbacks of the prior art, one object of the present invention is to provide a material having improved fluid management capabilities, in particular in regard to transporting fluid away from the point-of-use, in particular in the treatment of wounds, wherein said material does not suffer from the disadvantages outlined above, or at least minimizes these disadvantages.

According to a first aspect of the invention, these and other objects are achieved through a composite material, preferably for use as or in a medical dressing, comprising:
  a first layer comprising an absorbent fiber material, wherein said first layer has a first side and a second side opposite said first side, said first side being adapted to face an area of application in use, preferably adapted to face a wound area,
  a second layer comprising an absorbent material, said second layer being arranged on said second side of said first layer,
  wherein a plurality of channels extends through the entire first layer, from said first side to said second side thereof, and further extends into at least a portion of said second layer, wherein said channels have an average diameter of from 0.01 mm to 3.00 mm, preferably from 0.05 mm to 2.00 mm, further preferably from 0.10 mm to 1.00 mm In the claims and the description, the terms "comprising" and "comprise(s)" do not exclude other elements or steps, and the indefinite article "a" or "an" does not exclude a plurality of elements or steps. For example, two or more layers of absorbent material may be present and/or two or more layers of absorbent fiber material. Furthermore, the composite material may comprise further layers and/or elements of different functionality.

The mere fact that certain measures are recited in mutually different dependent claims does not indicate that a combination of these measured cannot be used to advantage.

In accordance with the present invention, the term "fiber" is to be understood as generally referring to threads or threadlike structures.

In accordance with the present invention, a "layer" is to be understood to have a continuous extension in one plane (x and y direction) and a thickness perpendicular to said plane (z direction), which thickness is typically less than the x-y-extension, preferably at least by a factor of 10.

In accordance with the present invention, the term "composite material" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to a multicomponent material comprising multiple, different (non-gaseous) phase domains, in which at least one type of phase domain is a continuous phase, preferably in which both phase domains are a continuous phase. In accordance with the present invention, the composite material comprises at least a first layer comprising an absorbent fiber material and at least a second layer comprising an absorbent material. For example, the second layer may be or comprise an absorbent foam material and/or may be or comprise an absorbent fiber material.

In accordance with the present invention, the term "absorbent" is to be understood as corresponding to the capability of a material to absorb a fluid in an amount of at least 3 times of its own weight, as measured in accordance with EN 13726-1:2002.

In embodiments of the invention, the absorbent fiber material is capable of absorbing and retaining a fluid. Therein, a "fluid retention capacity" is defined as the capability of a material (e.g. the absorbent fiber material) to retain aqueous saline solution, having first absorbed a maximum amount of 0.9% by weight aqueous saline solution according to EN 13726-1:2002, when exposed to a pressure of 40 mmHg for two minutes. The fluid retention capacity given in percentage (%) corresponds to the amount of residual moisture divided by the maximum absorption as determined according to EN 13726-1:2002.

In embodiments of the invention, the first layer has a retention capacity of at least 50%, preferably at least 60%, further preferably at least 70% wherein said fluid retention capacity is defined as described above.

In embodiments of the invention, the first layer is characterized by a fluid retention capacity of at least 80%. In embodiments of the invention, the first layer is characterized by a fluid retention capacity of at least 90%, or at least 95%.

A high retention capacity is inter alia useful if the composite material is used as or in a wound dressing, in particular, if the composite material is in direct contact with a wound or wound site. Generally, a high retention capacity of the hydrophilic fiber material lowers the risk of leakage and e.g. skin maceration as more liquid is contained within the composite material even when subjected to an outside pressure.

In embodiments of the invention, the first layer comprising the absorbent fiber material is characterized by a free swell absorptive capacity, corresponding to the maximum absorptive capacity, of at least 2 times its own weight as measured by EN 13726-1:2002, preferably at least 3 times its own weight as measured by EN 13726-1:2002 and more preferably at least 4 times or at least 5 times as measured by EN 13726-1:2002.

In embodiments of the invention, the absorbent fiber material is capable of absorbing and retaining a liquid by the formation of a hydrogel ("gelling fibers"), upon contact with a fluid, in particular an aqueous liquid. The term forming a "hydrogel" as used in accordance with the present invention, should be understood as relating to the formation of a polymer network in particular a network formed by cross-linking polymer or by nonlinear polymerization, which network is expanded throughout its whole volume by incorporation of a fluid, in particular an aqueous liquid, relative to the volume that the same polymer network would have without the presence of said fluid.

In embodiments of the invention, the first layer comprising an absorbent fiber material that is or comprises at least one polymer selected from the group consisting of polyvinyl alcohol (PVA), preferably cross-linked PVA, polysaccharides such as in particular cellulose and derivatives thereof, and polyacrylic acids.

Preferably, the cellulose polymer may be selected from the group consisting of carboxymethyl cellulose, carboxyethyl cellulose, hydroxymethyl cellulose, hydroxyethyl cellulose, hydroxypropyl cellulose, hydroxypropylmethyl cellulose; chitosan or deacetylated chitin, and algal polysaccharides.

In embodiments of the invention, the first layer comprising an absorbent fiber material is or comprises cross-linked polyvinyl alcohol or carboxymethyl cellulose (CMC). In embodiments of the invention, the at least one polymer is or comprises cross-linked PVA or CMC. In embodiments of the invention, the absorbent fiber material of the first layer is or comprises cross-linked polyvinyl alcohol. In embodiments of the invention, the polyvinyl alcohol (PVA) is cross-linked, preferably by heat treatment. In embodiments of the invention, the hydrophilic fiber material is or comprises carboxymethyl cellulose.

One suitable method of producing polyvinyl alcohol (vinyl alcohol does not exist as a monomer, at least not in quantities and purity that makes polymerization to PVA feasible) involves polymerization of vinyl acetate and subsequently hydrolyzing the resultant polyvinyl acetate to give polyvinyl alcohol. In some cases the degree of hydrolysis is not 100%, although a high degree of hydrolysis (e.g. at least 95 mol %) is typically preferred to ensure high hydrophilicity of the polymer and fibers including the polymer. Thus, in accordance with the present invention, it should be understood that "polyvinyl alcohol" or "PVA" may also include a degree of acetate (i.e. vinyl acetate units) in the polymer backbone.

In embodiments of the invention, the absorbent fiber material comprises a polyvinyl alcohol copolymer. For example, polyvinyl alcohol can be modified by copolymerization with other monomers. Preferably, polyethylene vinyl alcohol, polyvinyl alcohol styrene, polyvinyl alcohol vinyl acetate, polyvinyl alcohol vinyl pyrrolidone, polyvinyl alcohol ethylene glycol and/or polyvinyl alcohol, especially preferably polyethylene vinyl alcohol, polyvinyl alcohol vinyl acetate, polyvinyl alcohol vinyl pyrrolidone, polyvinyl alcohol vinyl amine, polyvinyl alcohol acrylate, polyvinyl alcohol acrylamide, polyvinyl alcohol ethylene glycol can be used as polyvinyl alcohol copolymers. The polyvinyl alcohol copolymers can be present in the form of block copolymers and/or graft copolymers and/or block graft copolymers, statistical or alternating systems and any mixtures of these with each other. The content of other monomer units in the polyvinyl alcohol is 30% at the maximum, preferably 1% to 30%, even more preferably 5% to 15%, each relative to the total number of monomer units in the polyvinyl alcohol copolymer.

In embodiments of the invention, the absorbent fiber material comprises a plurality of fibers configured to be able to hydrogel, wherein the plurality of fibers are produced from water-soluble polyvinyl alcohol, polyvinyl alcohol copolymer, or water-soluble polyvinyl alcohol and polyvinyl alcohol copolymer, and wherein hydrogelling is achieved by heat treatment of said plurality of fibers, such as the plurality of fibers disclosed in US 2013/0323195 and/or US 2013/0274415, the content of which relating to fiber materials is hereby incorporated by reference.

In embodiments of the invention, the absorbent fiber material comprises a polyurethane polymer with polyethylene glycol (PEG) and/or polypropylene glycol functionalities, such as the polymer fibers disclosed in WO 2013/041620.

One example of an absorbent fiber formed from polyacrylic acid is 'SAF'™, commercially available fibres sold by Technical Absorbent Limited (Grimsby, UK). SAF™ is formed from a cross-linked polymer of acrylic acid (AA) methylacrylate (MA) and a small quantity of special acrylate/methylacrylate monomer (SAMM) in which the acrylic acid is partially neutralized to the sodium salt of acrylic acid (AANa). SAF™ fibres are available in different staple lengths, linear density and with different degrees of cross linking to give different absorbency levels.

The term "cross-linked" is used herein to describe a material comprising a plurality polymer molecules which are interlinked by a chemical bond, in particular a covalent bond or an ionic bond, or by a physical cross-link, such as in thermoplastic elastomers.

The present invention is at least partly based on the realization that an absorbent fiber layer having a generally continuous extension in one plane (x-, y-direction), may have limited fluid transportation in the generally vertical direction of the layer (z-direction, i.e. direction of the extension of the thickness), in particular to an adjacent absorbent layer.

One particular advantage of the present invention is that fluid transportation in the vertical direction of an absorbent fiber layer is significantly improved by the provision of channels that extend not only through the absorbent fiber layer but also through at least a part of an adjacent layer, thereby providing a fluid path also across interfacial areas or surfaces thereof. These paths with supplement or even replace already existing fluid transport paths in a fibrous and/or porous material, which may be closed or obstructed during use, which is typically associated with the uptake of a fluid, for example a wound exudate, thus leading to a swelling of the absorbent material, reducing or eliminating the cross-section of fluid transport paths.

In embodiments of the invention, the second layer is in immediate physical contact with at least part of the second side of the first layer, preferably wherein the second layer is bonded to the second side of the first layer by at least one of chemical bonding or physical bonding. "Chemical bonding" refers to any binding of one layer to another by way of formation of chemical bonds, i.e. by way of chemical reaction (including any curing), in the course of which, in particular, covalent bonds are formed. By contrast, in "physical bonding", no chemical bonds are formed but rather the molecules making up the two layers interact with each other by way of interaction, in particular via (partial) charges, van der Waals forces and the like.

In accordance with the present invention, the term "immediate physical contact" is to be understood as relating to any contact between two layers so that a liquid can flow from one layer to the other by way of gravity, capillary forces, diffusion or the like, without the need of applying outside forces to (re)establish fluid flow.

In embodiments of the invention, the composite material further comprises an adhesive material at the interface between the first and the second layer, thereby adhering the two layers together. For example, a layer of any suitable adhesive material may be provided between the first and the second layer. Examples of suitable adhesive material include e.g. acrylates, hot-melt adhesives, polyurethane adhesives and silicone based adhesives.

In embodiments of the invention, the absorbent material of the second layer, is a hydrophilic material, preferably a hydrophilic foam material.

In accordance with the present invention, the term "hydrophilic" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to the capacity of a molecular entity or of a substituent to interact with polar solvents, in particular with water, or with other polar groups. Preferably, the term "hydrophilic" refers to the water-permeability property of a material or the water-attracting property of a molecule. In the context of a material with pores (such as, for example, open-cell foams) or materials with through-holes, such a material is "hydrophilic" if the material wicks up water. In the context of a material without pores or any through-holes, such a material is considered "hydrophilic" if it essentially does not resist the flow of water into or through the material.

In embodiments of the invention, the second layer comprising an absorbent material is characterized by a free swell absorptive capacity, corresponding to the maximum absorptive capacity, of at least 3 times its own weight as measured by EN 13726-1:2002, preferably at least 5 times its own weight as measured by EN 13726-1:2002 and more preferably at least 8 times or at least 10 times as measured by EN 13726-1:2002.

In embodiments of the invention, the second layer has a retention capacity of at least 30%, such as at least 40%, preferably at least 50% or at least 60%, more preferably at least 70% or at least 80% wherein said fluid retention capacity is defined as the capability of retaining aqueous saline solution, having first absorbed a maximum amount of 0.9% by weight aqueous saline solution according to EN 13726-1:2002, when exposed to a pressure of 40 mmHg for two minutes.

In embodiments of the invention, the second layer comprising an absorbent material comprises or is a hydrophilic polyurethane foam.

In embodiments of the invention, the hydrophilic foam is or comprises polyurethane polymer, preferably wherein the polyurethane foam material is obtained from a prepolymer comprising or being an isocyanate-capped polyol or isocyanate-capped polyurethane.

In embodiments of the invention, said polyol is selected from the group consisting of polyester polyols, polyacrylate polyols, polyurethane polyols, polycarbonate polyols, polyether polyols, polyesterpolyacrylate polyols, polyurethane polyacrylate polyols, polyurethane polyester polyols, polyurethane polyether polyols, polyurethane polycarbonate polyols and polyester polycarbonate polyols, among others, in particular polycondensates of di or optionally tri-, and tetraols as well as di or optionally tri- and tetracarboxylic acids or hydroxycarboxylic acids or lactones.

Exemplary suitable diols are ethylene glycol, butylene glycol, diethylene glycol, triethylene glycol, polyalkylene glycols such as polyethylene glycol, and also 1,2-propanediol, 1,3-propanediol, 1,3-butanediol, 1,4-butanediol, 1,6-hexanediol and isomers, neopentyl glycol or neopentyl glycol hydroxypivalate, In addition, polyols such as trimethylolpropane, glycerol, erythritol, pentaerythritol, trimethylolbenzene or trishydroxyethyl isocyanurate are also within the scope of the present invention.

In embodiments of the invention, said polyol is a polyethylene glycol (polyethylene oxide). Accordingly, in embodiments of the invention, the prepolymer is or comprises an isocyanate-capped polyethylene glycol.

In embodiments of the invention, the prepolymer derives from a reaction between said polyol and a diisocyanate compound selected from the group consisting of hexamethylene diisocyanate (HDI), toluene diisocyanate (TDI), methylene diphenyl diisocyanate (MDI), or isophorone diisocyanate (IPDI), or any mixture thereof.

In embodiments of the invention, the prepolymer derives from a reaction between said polyol and a diisocyanate compound that is aliphatic. In embodiments of the invention, the diisocyanate compound is or comprises hexamethylene diisocyanate (HDI). Accordingly, in embodiments of the invention, the prepolymer is or comprises an hexamethylene isocyanate-capped polyol or hexamethylene isocyanate-capped polyurethane.

In embodiments of the invention, the prepolymer is or comprises a hexamethylene isocyanate-capped polyethylene glycol.

In embodiments of the invention, the prepolymer derives from a reaction between said polyol and a diisocyanate compound that is aromatic. In embodiments of the invention, the diisocyanate compound is or comprises toluene diisocyanate (TDI), methylene diphenyl diisocyanate (MDI). Accordingly, in embodiments of the invention, the prepolymer is or comprises a toluene isocyanate-capped polyol or a methylene diphenyl isocyanate-capped polyol or toluene isocyanate-capped polyurethane or methylene diphenyl isocyanate-capped polyurethane.

In embodiments of the invention, the prepolymer is or comprises a toluene isocyanate-capped polyethylene glycol. In embodiments of the invention, the prepolymer is or comprises a methylene diphenyl isocyanate-capped polyethylene glycol.

In embodiments of the invention, the polyurethane foam material is an open-cell porous hydrophilic foam having a density of 60 to 180 kg/m$^3$ as measured according to standard method ISO 845:2006, preferably a polyurethane foam material of that density, preferably 100 to 150 kg/m$^3$, as measured according to standard method ISO 845:2006.

As used herein, the term "open-cell" refers to the pore structure of the foam, wherein the pores in an open-cell pore structure are connected to each other and form an interconnected network.

In accordance with the present invention, the term "prepolymer" is to be understood as defined in IUPAC: Compendium of Chemical Terminology, 2nd ed. (the "Gold Book"), compiled by A. D. McNaught and A. Wilkinson. Blackwell Scientific Publications, Oxford (1997), ISBN 0-9678550-9-8, as generally referring to a polymer or oligomer the molecules of which are capable of entering, through reactive groups, into further polymerization and thereby contributing more than one structural unit to at least one type of chain of the final polymer.

An important aspect of the present invention is that a plurality of channels extends through the entire first layer, from said first side to said second side thereof, and further extends into at least a portion of said second layer.

In accordance with the present invention, the term "channel" is to be understood as referring to generally open structures, i.e. structures that allow for the through-flow of fluids (liquids or gases) and, unless filled with a fluid during the intended use, are not obstructed by the material making up the layer, in particular the absorbent fiber material. In embodiments, these channels are "open" in the above-described sense over essentially their entire length.

In particular, while these channels may be filled with fluid during intended use, these channels retain an open structure in the sense that the channels are not permanently closed to liquid flow during use, including during use in the presence of materials that may increase in density during use, for example due to swelling/forming of a hydrogel.

It is understood that the (average) diameter of these channels may increase or (more typically) decrease during use, but not to an extent that essentially all channels are closed to essentially all fluid flow. In embodiments of the invention, the channels are characterized by an aspect ratio, i.e. ration of (average) open length to (average) open diameter of at least 1:1, preferably at least 2:1, further preferably at least 5:1.

In embodiments of the invention, said channels are arranged essentially perpendicular to the first layer and the second layer, and therefore also essentially perpendicular to the interface between those two layers.

In embodiments of the invention, no channels are present in at least 20%, preferably in at least 30%, of the overall area of the first side of the first layer. For example, in embodiments of the invention, the overall area of the first side of the first layer comprises a first central portion and second portion surrounding the first portion, wherein channels are only present in the first central portion, and wherein the area of the second portion is at least 20% of the overall area of the first side of the first layer.

In embodiments of the invention said channels are arranged in patterns.

In embodiments of the invention, said channels form a continuous pattern of square(s) on the area of the first side of the first layer, or of circle(s) growing out from the center of the area of the first side of the first layer, In other embodiments, the channels form ornamental or informative patterns, such as waves or text communicating a message.

In embodiments of the invention at least a part of said channels has a diameter that varies along its length and/or at least one subset of channels has a diameter that is different from the diameter of another subset of channels.

In embodiments of the invention, the area density of channels per overall area of said first side of said first layer, is from 0.5 channel per square centimeter to 200 channels per square centimeter, preferably from 1 channel per square centimeter to 100 channels per square centimeter, more preferably 1 channel per square centimeter to 50 channels per square centimeter.

The above-described embodiments of channels, alone or in combination, allow to adjust the fluid directing properties to the specific situation at hand, for example specific fluid viscosity, specific flow rate, specific intended use etc.

In embodiments of the invention, the first layer has a thickness of from 0.2 mm to 3 mm, preferably from 0.5 mm to 2 mm.

In embodiments of the invention, the second layer has a thickness of from 250 µm to 30 mm, preferably from 1 mm to 10 mm, further preferably from 2 mm to 7 mm.

In accordance with the invention, the term "thickness" of a layer is to be understood as measured according to EN ISO 9073-02.

In embodiments of the invention, the first layer and/or the second layer comprise(s) a first sublayer and a second sublayer.

In embodiments of the invention, the absorbent fiber material of the first layer may entirely consist of or comprise a non-woven material.

In accordance with the present invention, the term "nonwoven" is to be understood as generally referring to any network of fibers that are held together by interlocking or bonding [in particular by chemical (solvent) or thermal means], and not by means of being woven or knitted.

In embodiments of the invention, the first layer has a basis weight of from 10 to 600 g/m². In embodiments of the invention, the first layer has a basis weight of from 50 to 400 g/m².

In embodiments of the invention, the first layer and/or the second layer comprise(s) an antimicrobial agent.

In embodiments of the invention, the antimicrobial agent comprises silver. In embodiments of the invention, the silver is metallic silver. In embodiments of the invention, the silver is a silver salt. In embodiments of the invention, the silver salt is silver sulfate, silver chloride, silver nitrate, silver sulfadiazine, silver carbonate, silver phosphate, silver lactate, silver bromide, silver acetate, silver citrate, silver CMC, silver oxide. In embodiments of the invention, the silver salt is silver sulfate. In embodiments of the invention, the antimicrobial agent comprises a monoguanide or biguanide. In embodiments of the invention, the monoguanide or biguanide is chlorhexidine digluconate, chlorhexidine diacetate, chlorhexidine dihydrochloride, polyhexamethylene biguanide (PHMB) or a salt thereof, or polyhexamethylene monoguanide (PHMG) or a salt thereof. In embodiments of the invention, the biguanide is PHMB or a salt thereof. In embodiments of the invention, the antimicrobial agent comprises a quaternary ammonium compound. In embodiments of the invention, the quaternary ammonium compound is cetylpyridinium chloride, benzethonium chloride, or polyDADMAC. In embodiments of the invention, the antimicrobial agent comprises triclosan, sodium hypochlorite, copper, hydrogen peroxide, xylitol, iodine, or honey.

In embodiments of the invention, the composite material is characterized by a free swell absorptive capacity, corresponding to the maximum absorptive capacity, of at least 3 times its own weight, preferably at least 5 times its own weight, for example at least 10 times its own weight, as measured by EN 13726-1:2002

According to a second aspect of the invention, the abovementioned and other objects are achieved by means of providing a medical dressing comprising the composite material according to the invention.

In embodiments of the invention, the first layer (of the composite material) is adapted to be in contact with the area of application, such as for example, a wound or wound site and/or peri-wound area and/or healthy skin. In embodiments of the invention, the first layer is the wound contact layer. In embodiments of the invention, the first side of the first layer is adapted to be in contact with a wound site.

In accordance with the present invention, the term "wound site" or "wound area" or "wound" is to be understood as any open or closed wound, for example, including inter alia (but not limited to) chronic wounds, acute wounds, and post-operative wounds such as e.g. closed incisions and scar treatment.

In embodiments of the invention, the medical dressing comprises the first layer and the second layer of the composite material, preferably in the form of a sequence of layers, wherein the medical dressing further comprises at least one further layer, preferably a backing layer overlaying said second layer and/or an adhesive layer or a coating to adhere said to a wound site and/or a periwound area, preferably two or more of these further layers.

In embodiments of the invention, the medical dressing is a wound dressing.

The embodiments, features and effects described above in connection with the composite material according to the first aspect of the invention are applicable, mutatis mutandis, for the above described medical dressing according to the second aspect of the invention.

According to a third aspect of the invention, the abovementioned and other objects are achieved by means of a method for producing a composite material, said method comprising the steps of:
(i) providing a first layer comprising an absorbent fiber material capable of absorbing and retaining a fluid, wherein the first layer has a first side and a second side opposite said first side, said first side being adapted to face the area of application in use,
(ii) providing, on said second side of said first layer, a second layer comprising an absorbent material,
(iii) creating a plurality of channels, extending through the entirety of the first layer, from said first side to said second side, and further extending into at least a portion of said second layer,
wherein said channels have an average diameter of from 0.01 to 3.00 mm, preferably from 0.05 to 2.00 mm, further preferably from 0.10 mm to 1.00 mm.

In embodiments of the invention, the channels are created by way of punching (e.g. using a rotating dye cut, or needles), heated pins, and/or laser beam application, for example.

In embodiments of the invention, the method further comprises a step of bonding together the first layer and the second layer. For example, the first and the second layer may be chemically bonded by means of covalent bonds or by direct physical interaction.

In embodiments of the invention, the method further comprise a step of adding an adhesive layer to one of the first and second layer before the step (ii) of providing a second layer on said first side of the first layer, thereby bonding the first and the second layer.

In embodiments of the invention, step (ii) as specified above, includes the step of bringing a second layer in immediate physical contact with the first side of said first layer, and subsequently bonding the first and the second layer together. For example, in embodiments of the invention, the second layer comprises a foam material and wherein the step of bonding two layers involves applying the first layer comprising an absorbent fiber material to a surface of a casted prepolymer composition (i.e. precursor of the foam material) such that the prepolymer composition reacts with the fiber material (e.g. alcohol or amine side groups) in situ during the foaming process of the second layer, and thus chemical (covalent) bonds are formed.

BRIEF DESCRIPTION OF THE DRAWINGS

These and other aspects of the invention will now be shown in more detail, with reference to the appended drawings showing exemplary embodiments of the invention, wherein.

DESCRIPTION OF EMBODIMENTS OF THE INVENTION

In the following description, detailed embodiments of the present invention are described, partly with reference to the accompanying drawings, which are exemplary illustrations of embodiments of the invention.

Figure 1:
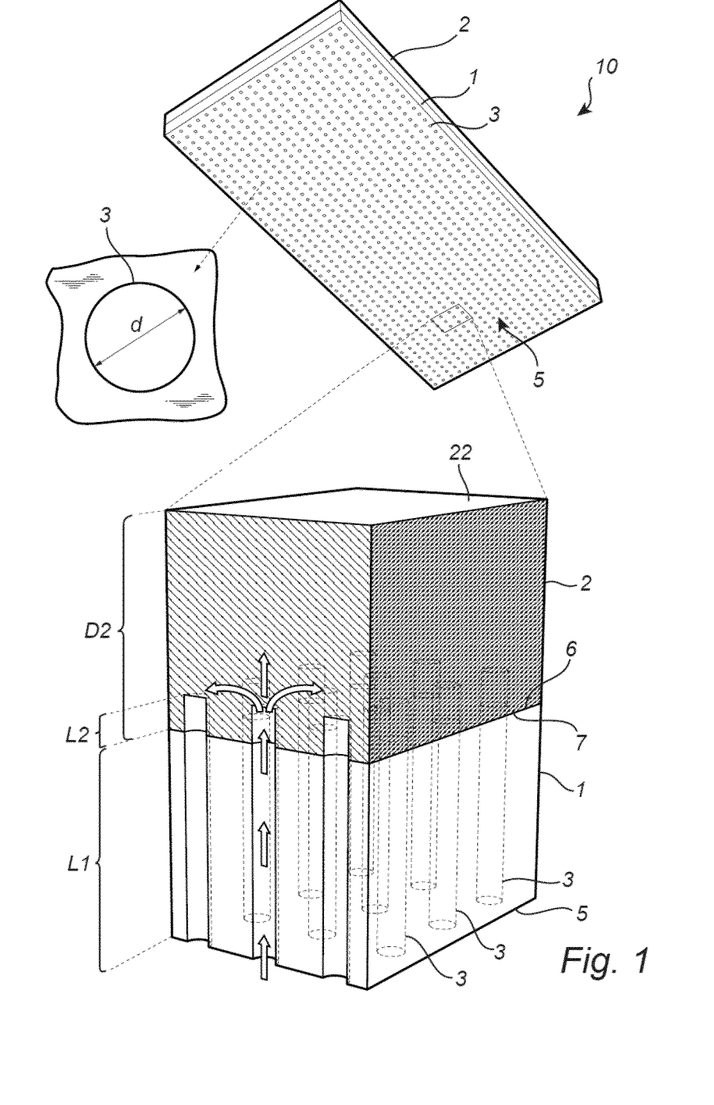
FIG. 1 is a schematic depiction of the composite material and the fluid management principle underlying the present invention.

FIG. 1 is a perspective view of an exemplary embodiment of a composite material according to the invention wherein the composite material comprises a first layer 1 comprising an absorbent fiber. The first layer 1 has a first side 5 and a second side 6 opposite the first side 5. The composite material further comprises a second layer 2 comprising an absorbent material, such as for example an absorbent foam material. The second layer 2 is arranged to be in contact with the second side 6 of the first layer 1, wherein a plurality of channels 3 extends through the entirety (L1) of the first layer 1 and into at least a part (L2) of the second layer 2.

As schematically illustrated in FIG. 1, the plurality of channels 3 facilitates fluid transport from the first side 5 of the first layer 1, through the thickness of the first layer 1, and across the interface between the first layer 1 and second layer 2 and into the core of the second layer 2. As shown in FIG. 1, a plurality of channels 3 extends in vertical direction (i.e. z-direction or direction of thickness perpendicular to the plane of the layer 1).

The inventor has realized that fluid transport through a layer 1 may be limited due to the potential for swelling and thus closing otherwise open fluid transport paths through the fiber network of layer 1, and that the same fluid transport can be significantly improved by providing a plurality of channels 3 that extends through the layer 1 and into an adjacent second layer 2. Thereby, the full absorption capacity of the composite material is utilized, as the fluid can be absorbed and retained in both the first and the second layer.

Exacerbating the already limited fluid transport due to swelling in the first layer 1, fluid transportation across an interface between two or more layers in a composite material 10 may be poor or limited, for example due to the presence of an adhesive layer or the material structure in the interfacial area. However, also this problem is addressed through the inventive composite material 10 as the plurality of channels 3 extend through at least part of the second layer 2 and therefore also through the interface between the layers 1, 2.

In embodiments of the invention, the plurality of channels 3 extends at least a distance L2 into the second layer 2, which distance L2 corresponds to at least 5%, preferably at least 15%, further preferably at least 25% of the total thickness D2 of the second layer.

FIGS. 2a-d illustrate exemplary embodiments of medical dressings 20, 30, 40, 50, comprising the composite material 10, as realized in the form of a sequence of layers 1, 2. The medical dressings, which may be wound dressings, 20, 30, 40, 50, shown in FIGS. 2a-d thus comprise the first layer 1 comprising an absorbent fiber material and the second layer 2 comprising an absorbent material, such as for example a hydrophilic polyurethane foam material, wherein a plurality of channels 3 extend through the entirety of the first layer 1 and extend into at least a part of the second layer 2.

In embodiments of the invention, the medical dressings 20, 30, 40, 50 further comprise a backing layer 21, 23 overlaying a top side 22 of the second layer 2, wherein the top side 22 is opposite to the side 7 facing the second side 6 of the first layer 1. Thereby, the first layer 1 has a first side 5 which can function as a direct or indirect wound contact layer, wherein the first layer 1 is adapted to provide initial absorption and retention of wound fluid and/or to transport wound fluid from the wound to the above second layer 2 through the plurality of channels 3 in the first layer 1.

It is typically desirable to transport wound fluid away from the wound site, in particular, in case of a high exuding wound it is paramount that wound fluid (e.g. wound exudate) can be transported to the layer (e.g. second layer 2) closest to the backing layer 21, 23 and subsequently be evaporated through the backing layer 21, 23, which layer is typically gas permeable but liquid impermeable. In use of the medical dressings 20, 30, 40, 50, the plurality of channels 3, provided in the first layer 1 having a first side 5 adapted to be facing the area of application (e.g. wound site), are in fluid communication with the wound site, thus facilitates wound exudate transport from the wound to the second layer 2 which in turn is in contact with the backing layer 21, 23.

Figure 2A:
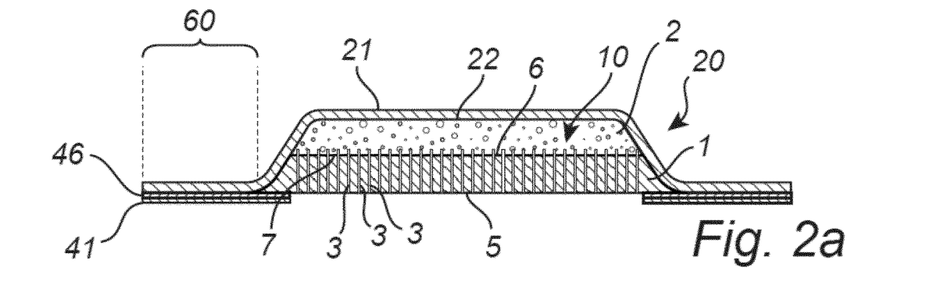
FIGS. 2a-d represent cross-sectional views of embodiments of a medical dressing according to the invention.
Figure 2B:
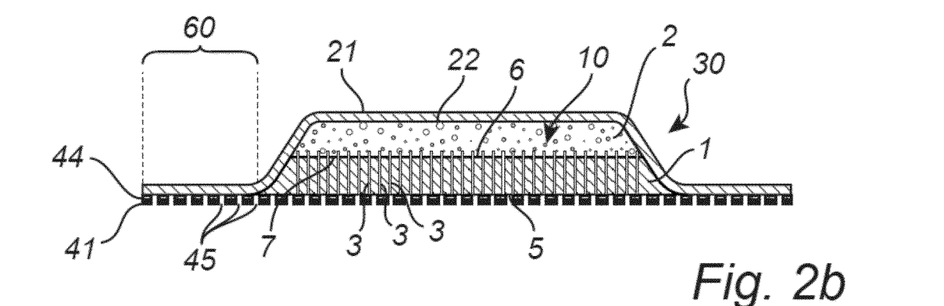

In embodiments of the invention, as shown in FIGS. 2a-b, the backing layer 21 extends outside the peripheral portion of the layers of the composite material 10, to define a border portion 60 of the backing layer 21 thus surrounding the peripheral portion of the layers 1, 2 of the composite material 10, thereby providing a so-called island dressing.

In embodiments of the invention, the backing layer 21, 23 is preferably vapor permeable. The backing layer 21, 23 may be a plastic film, for example, comprising or consisting of polyurethane, polyethylene, or polypropylene. In embodiments of the invention, the backing layer 21, 23 is a polyurethane film having a thickness in the range of 10-100 μm, for example, 10-80 μm such as 10-50 μm.

Figure 2C:
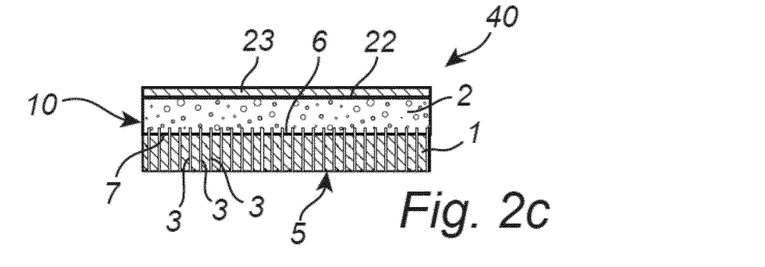
Figure 2D:
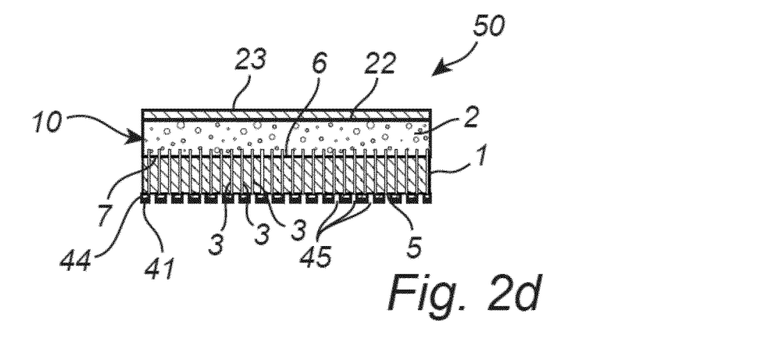

As schematically illustrated in FIG. 2a, FIG. 2b and FIG. 2d, the wound dressings 20, 30, 50, include an adhesive layer or coating 41 to adhere the medical dressings 20, 30, 50 to a wound and/or the surrounding skin surface. In embodiments of the invention, the adhesive layer or coating 41 may be a silicone based adhesive or an acrylic based adhesive, preferably the adhesive layer or coating is a silicone based adhesive. The term "coating" should, in accordance with the present invention, be understood as at least one continuous layer on a surface, or a discontinuous cover on a surface e.g. plurality of particles distributed on an area of a surface.

In embodiments of the invention, as depicted in FIG. 2c, the medical dressing 40 is a non-adherent dressing which may, for example, be attached to an area of application (e.g. wound site or skin) by any attaching means such as medical tapes and/or be used together with a secondary adhesive dressing.

As shown in FIG. 2b and FIG. 2d, the wound dressings 30, 50 may include a perforated layer 44, for example made of a polyurethane film, wherein an adhesive coating 42 is provided on the non-perforated portions of the perforated layer 44. The perforated layer 44 includes a plurality of openings 45 (or through holes) of any desirable size and shape. The shape and size of the openings 45 may be adapted to achieve a desirable liquid transport from the wound to the above layers of the composite material 10, for example, to the plurality of channels 3.

In embodiments of the invention, as illustrated in FIG. 2b, the perforated layer 44 with the adhesive coating 41 is provided on the first side 5 of the first layer 1, wherein the perforated layer 44 extends outside the peripheral portion of the layers of the composite material 10 and is attached to the border portion 60 of the backing layer 21.

In alternative embodiments, as shown in FIG. 2d, the footprint of the perforated layer 44 corresponds to the footprint of the composite material 10. In embodiments of the invention, as shown in FIG. 2a, an adhesive coating 41 is provided on a continuous plastic film 46, for example a polyurethane film as discussed above, which continuous plastic film 46 is arranged adjacent to a peripheral portion of the layers of the composite material 10, wherein the continuous film 46 extends away from said peripheral portion and is attached to the border portion 60 of the backing layer 21. In further embodiments (not shown) an adhesive coating may be provided directly on a skin facing surface of the border portion 60 of the backing layer 21.

In embodiments of the invention, the first layer 1 and/or the second layer 2 comprise(s) a first sublayer and a second sublayer (not shown). For example, the first layer 1 may include a first sublayer of a non-woven absorbent layer and a second sublayer comprising absorbent fibers or particles. For example, the first sublayer may be a non-woven layer covalently bonded to the second layer 2 which may comprise an hydrophilic polyurethane material, and the second sublayer may comprise a mixture of superabsorbent fibers and/or superabsorbent particles and/or non-absorbent fibers, which mixture may be airlaid, e.g. by spraying, needling, or carding, on a side of the first sublayer opposite to the side bonded to the foam layer.

The terms "superabsorbent fibers" or "superabsorbent particles" as used in accordance with the present invention are generally understood to be water-swellable, water-insoluble organic or inorganic materials capable of absorbing at least about 20 times their own weight as measured by EN 13726-1:2002. Organic materials suitable for use as a superabsorbent material preferably include natural materials such as polysaccharides (including modified polysaccharides such as carboxymethyl cellulose (CMC)), polypeptides and the like, as well as synthetic materials such as synthetic hydrogel polymers. Such synthetic hydrogel polymers include, for example, alkali metal salts of polyacrylic acids, polyacrylamides, polyvinyl alcohol, polyacrylates, polyvinyl pyridines.

The invention is further illustrated in the following Examples. Unless otherwise specified, all experiments and tests described herein were performed at standard laboratory conditions, in particular at room temperature (20° C.) and standard pressure (1 atm.).

EXAMPLE 1

Materials Used

Exufiber® (size 10×10 cm; Product code: REF 603301; LOT: 16064983; Use by: 2019-05); commercially available from Mölnlycke Health Care (absorbent fiber material);

Lyofoam® Max (size 10×10 cm; REF 603201-00; LOT 15108622; Use by: 2018-09); commercially available from Mölnlycke Health Care; (absorbent foam);

Display Mount™ Adhesive (spray adhesive; 140A02PL6; EXP2017/05; MSDS No. 27-7170-7/16.06.2014); commercially available from 3M.

Preparation of Embodiments

The spray adhesive was applied on the foam side of the Lyofoam® Max product from a distance of 20 cm, in two application steps. The adhesive spray coating was rested for 30 seconds before the Exufiber® product was applied on the adhesive coating by hand.

One approach to estimate the adhesive amount was made by spraying a thin plastic film (pre-weighted) in the same way as the Lyofoam® Max product and subsequently the coated film was weighted, and the adhesive coating weight was calculated to be ca. 2.2 gsm. This should only be understood as a reasonable estimate of the amount of adhesive used but clearly indicates that a comparatively low amount of adhesive has been applied. As the plastic film is transparent, it was also observed (visually) that the adhesive coating is not fully covering the surface but provides an open structure.

Channels were subsequently introduced into the material, using a laser platform (V-460; Universal Laser System, system setting: Laser Template Power 100% and Speed 3.5%). The laser was applied to the fiber side of the composite embodiment such that channels were created extending through the entire fiber layer and approximately into 50% of the thickness of the foam layer. Two embodiments of the invention, were thus prepared each having channels with different average diameter: 0.25 mm (embodiment A) and 0.75 mm (embodiment B), respectively.

The embodiment A, with an average channel diameter of 0.25 mm, was designed so that the channel density was 17.3 channels/cm$^2$ (108 (9×12) channels per 6.25 cm$^2$), wherein embodiment B, with an average channel diameter of 0.75 mm, was designed so that the channel density was 4.8 channels/cm$^2$ (120 (10×12) channels per 25 cm$^2$).

A reference embodiment C without any channels was also prepared using the same material and methods as described above (except the step of introducing channels).

EXAMPLE 2

Test of Absorption Capacity/Distribution of Liquid

The absorption capacity was tested using an inclined plane with 60° inclination according to a test method described in detail below. The purpose of the test method is to determine the absorption capacity of, and liquid distribution in, materials exposed to compression and gravity when a test liquid is added at a constant flow rate, e.g. one intention of the test is to mimic a wound treatment situation.

Figure 3:
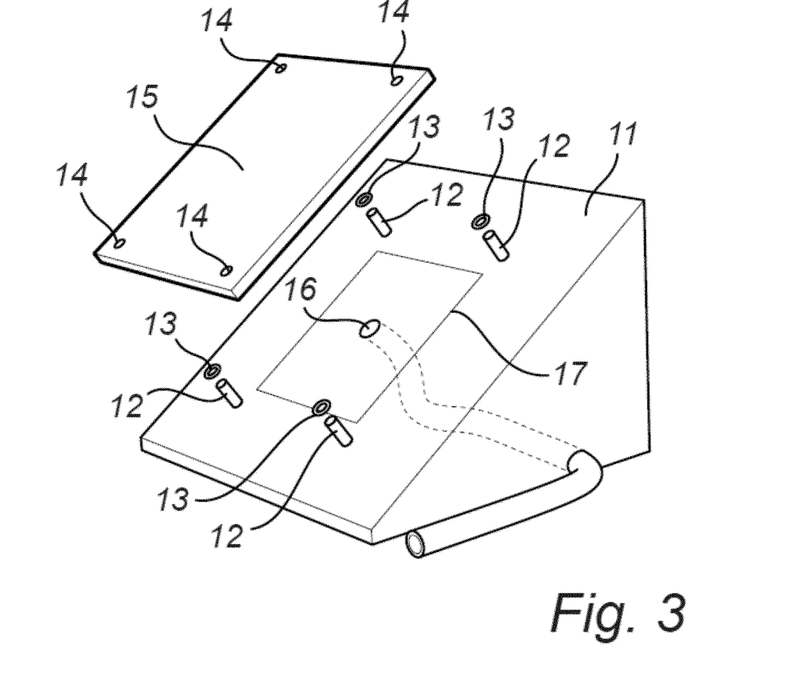
FIG. 3 is a schematic depiction of the 60° inclined plane test apparatus used in the absorption capacity/fluid distribution test as developed by Applicant.

General Description of Test Method:

An inclined plane test device as illustrated in FIG. 3 was used, wherein the test device includes an inclined test plate 11 (typically made of Plexiglas) fixed in a 60 degree inclination. Before starting the test, the following preparations are made: 1) the syringe pump is loaded with test liquid (Solution A according to EN 13726-1) including the tube all the way to the outlet hole 16; 2) a test piece with the size 100×100 mm is cut out; 3) using a thickness meter the thickness corresponding to an applied pressure of 4 mmHg (on the test piece) is measured (the weight corresponding to this pressure on a 100×100 mm test piece is a total of 544 g); 4) the test piece (i.e. one of the prepared embodiments; 100×100 mm) is applied on the inclined test plate 11 such that the fiber (Exufiber®) side is facing the test plate. As shown in FIG. 3, the inclined test plate 11 is marked with a 100×100 mm square 17 centred over the liquid outlet 16 to show where the test piece should be positioned; 5) spacers 13, corresponding to the measured thickness (as measured by the thickness meter), are inserted on the screws 12 such that the correct distance to achieve a pressure of 4 mmHg (on the test piece) is ensured; and 6) the covering plate 15 (typically made of Plexiglas) is attached onto the inclined test plate 11 by inserting the screws 12 into the holes 14 of the covering plate 15 and tighten with screw nuts on the screws (thereby sandwiching test piece between the two plates 11, 15).

The test liquid (Solution A as defined in EN 13726-1) is added through the outlet 16 into the centre of test piece from underneath (i.e. to the fiber side) at a constant flow rate of 5 ml/h (using a Dosimat/syringe pump). The test is performed for a period of 2 hours (unless leakage occurs in which case the test is stopped).

Results

Embodiment A and reference embodiment C were tested in the above described test method. The absorption of Solution A was monitored over time at 3 ml, 7 ml, and 10 ml of added Solution A, by measuring the wetted/absorption area on both sides of the embodiments (e.g. Exufiber® side and foam side). The area was visually inspected, recorded and measured by drawing a line, corresponding to the wetted area, on a transparent overhead film. The drawn area on the film was subsequently cut out and weighted to give the area of absorption (as reference the weight per cm$^2$ of the film is used). The ratio of the measured absorption area (Exufiber® side/Lyofoam® Max side) for each measurement is presented in Table 1 below. It should be further noted that three test pieces of each embodiment (A and reference C) were used and the result (highlighted in bold) presented herein is the calculated average value.

TABLE 2

| Embodiment | Spec. | Exufiber® (g) | Lyofoam® Max (g) | Ratio Exufiber®/ Lyofoam® Max |
|---|---|---|---|---|
| A | 1 | 6.7 | 10.3 | 0.90 |
|  | 2 | 6.8 | 10.2 | 0.94 |
|  | 3 | 7.3 | 10.7 | 0.93 |
|  |  |  |  | 0.9 |
| C | 1 | 7.7 | 9.1 | 1.39 |
|  | 2 | 7.1 | 9.8 | 1.03 |
|  | 3 | 7.8 | 9.4 | 1.32 |
|  |  |  |  | 1.2 |

It should be noted that at least some test liquid that has been transported to, and absorbed by, the foam layer, may be transported back to the fiber layer wetting the fiber side facing the foam layer) over time, in particular since the Exufiber® fiber layer has higher liquid retention capacity vis-à-vis the Lyofoam® Max foam layer. Without wishing to be bound by theory, this may explain why a larger difference in liquid distribution between embodiment A and reference embodiment C is observed in the beginning of the test (e.g. at 3 ml).

TABLE 1

| | | Area (cm$^2$) at 3 ml | | | Area (cm$^2$) at 7 ml | | | Area (cm$^2$) at 10 ml | | |
|---|---|---|---|---|---|---|---|---|---|---|
| Embodiment | Spec. | Exufiber® | Lyofoam® Max | Ratio Exufiber®/ Lyofoam® Max | Exufiber® | Lyofoam® Max | Ratio Exufiber®/ Lyofoam® Max | Exufiber® | Lyofoam® Max | Ratio Exufiber®/ Lyofoam® Max |
| A | 1 | 14.2 | 3.4 | 4.1 | 22.2 | 18.9 | 1.2 | 26.7 | 21.7 | 1.2 |
|  | 2 | 15.9 | 2.3 | 7.0 | 23.9 | 14.9 | 1.6 | 28.4 | 18.3 | 1.6 |
|  | 3 | 13.1 | 3.4 | 3.8 | 23.3 | 16.0 | 1.5 | 31.3 | 23.4 | 1.3 |
|  |  |  |  | 5.0 |  |  | 1.4 |  |  | 1.4 |
| C | 1 | 16.0 | 0.0 | N/A | 32.0 | 6.9 | 4.7 | 33.7 | 12.6 | 2.7 |
|  | 2 | 16.0 | 0.6 | 28.0 | 26.3 | 12.6 | 2.1 | 30.9 | 18.3 | 1.7 |
|  | 3 | 18.3 | 0.3 | 64.0 | 32.6 | 6.3 | 5.2 | 36.0 | 12.6 | 2.9 |
|  |  |  |  | 46.0 |  |  | 4.0 |  |  | 2.4 |

The test liquid is added to the fiber side of the composite material in the test method as described above. As can be seen in Table 1, there is a distinct difference in absorption between the two embodiments tested, in particular with regard to liquid distribution and transportation of test liquid from the fiber layer to the above foam layer. After 3 ml of added test solution most of the added test liquid, if not all, has been absorbed by the fiber layer in reference embodiment C, as opposed to embodiment A wherein a substantial amount of test liquid has been transported into the foam layer. Also after 7 ml and 10 ml, respectively, of added test liquid, it can be seen that embodiment A has a higher distribution of test liquid in the foam layer as compared with reference embodiment C. This clearly illustrates the technical effect of the channels present in embodiment A which function to facilitate transport of test liquid from the liquid acquisition fiber layer across the interface of the two layers and into the foam layer, whereas reference embodiment C does not include any channels and therefore less test liquid can be transported through the gelling fiber layer.

In the same test as presented above, at the end of the test (i.e. at 10 ml of added Solution A), the two layers of the composite (Exufiber® and Lyofoam® Max) were separated and weighted. Table 2 below shows the corresponding weights and weight ratios. As can be seen in Table 2, embodiment A has a higher distribution of test liquid in the foam layer as compared with reference embodiment C.

The invention claimed is:

1. A composite material comprising:
    a first layer comprising an absorbent fiber material, wherein said first layer has a first side and a second side opposite said first side, said first side being adapted to face an area of application in use,
    a second layer comprising an absorbent material that comprises or is a hydrophilic foam, wherein said second layer has a thickness, said second layer being arranged on said second side of said first layer,
    wherein a plurality of channels extends through the entire first layer, from said first side to said second side thereof, and further extends into a portion of the thickness of said second layer, wherein said plurality of channels does not extend through the total thickness of the second layer, wherein said channels have an average diameter of from 0.01 mm to 3.00 mm.

2. The composite material according to claim 1, wherein said fiber material is capable of forming a hydrogel when brought into contact with water.

3. The composite material according to claim 1, wherein said second layer is in immediate physical contact with at least part of said second side of said first layer.

4. The composite material according to claim 1, wherein said composite material further comprises an adhesive material at the interface between said first layer and said second layer.

5. The composite material according to claim 1, wherein said channels are arranged essentially perpendicular to said first layer and said second layer, and the interface between those two layers.

6. The composite material according to claim 1, wherein no channels are present in at least 20% of the overall area of said first side of said first layer.

7. The composite material according to claim 1, wherein said channels are arranged in patterns.

8. The composite material according to claim 1, wherein said first layer has a fluid retention capacity of at least 50%, wherein said fluid retention capacity is defined as the capability of retaining aqueous saline solution, having first absorbed a maximum amount of 0.9% by weight aqueous saline solution according to EN 13726-1:2002, when exposed to a pressure of 40 mmHg for two minutes.

9. The composite material according to claim 1, wherein at least a part of said channels has a diameter that varies along its length and/or wherein at least one subset of channels has a diameter that is different from the diameter of another subset of channels.

10. The composite material according to claim 1, wherein the area density of channels per overall area of said first side of said first layer, is from 0.5 channel per square centimeter to 200 channels per square centimeter.

11. The composite material according to claim 1, wherein said first layer is or comprises a non-woven material.

12. The composite material according to claim 1, wherein said absorbent fiber material comprises at least one polymer selected from the group consisting of polyvinyl alcohol, a polysaccharide, cellulose and derivatives thereof, carboxymethyl cellulose, and polyacrylic acids.

13. A medical dressing comprising a composite material according to claim 1, wherein said first layer is adapted to be in contact with a wound site.

14. The medical dressing according to claim 13, wherein said medical dressing further comprises at least one further layer being a backing layer overlaying said second layer and/or an adhesive layer or a coating to adhere said medical dressing to a wound site and/or a periwound area.

15. A method for producing a composite material according to claim 1, said method comprising the steps of:
(i) providing the first layer comprising an absorbent fiber material, wherein said first layer has a first side and a second side opposite said first side, said first side being adapted to face the area of application in use,
(ii) providing, on said second side of said first layer, a second layer comprising an absorbent material that comprises or is a hydrophilic foam, wherein said second layer has a thickness,
(iii) creating a plurality of channels, extending through the entirety of said first layer, from said first side to said second side, and further extending into a portion of the thickness of the second layer, wherein said plurality of channels does not extend through the total thickness of the second layer, wherein said channels have an average diameter of from 0.01 mm to 3.00 mm.

* * * * *